United States Patent [19]

Kennedy et al.

[11] Patent Number: 4,969,741
[45] Date of Patent: Nov. 13, 1990

[54] MEASUREMENT OF SOLID PARTICLE CONCENTRATION IN PRESENCE OF A SECOND PARTICLE TYPE

[75] Inventors: Max J. Kennedy, Cambridge; Daniel I. C. Wang, Belmont; Gregory N. Stephanopoulos, Winchester, all of Mass.

[73] Assignee: Massachusetts Institute of Technology, Cambridge, Mass.

[21] Appl. No.: 383,798

[22] Filed: Jul. 21, 1989

[51] Int. Cl.$^5$ .................. G01N 21/00; G01N 15/02
[52] U.S. Cl. ................... 356/338; 356/335; 356/301
[58] Field of Search ................ 356/335–343, 356/73, 39, 301, 319, 323, 325, 326; 250/564, 565; 435/291, 808, 173

[56] References Cited

U.S. PATENT DOCUMENTS

| | | | |
|---|---|---|---|
| 2,344,748 | 3/1944 | Stearns, Jr. | 356/323 |
| 3,954,336 | 5/1976 | Baird et al. | 356/73 |
| 4,768,879 | 9/1988 | McLachlan et al. | 356/335 |

OTHER PUBLICATIONS

Kennedy, M. et al., *Amer. Chem. Soc.* 196th Meeting, Los Angeles, Microbiol. and Biochemical Abstract #159, (Jul. 22, 1988).
Hancher, C. et al., *Biotech. Bioeng.* 16:475–484 (1974).
Powell, E. O., *J. Sci. of Food and Agric.* 14:1–8 (1963).
Junker, B. et al., *Biotech. Bioeng.* 32:55–63 (1988).
Clarke, D. et al., *Trends in Biotech.* 4:173–178 (1986).
Taya, M. et al., *J. Ferment. Technol.* 64:411–417 (1986).
Lee, Y., *Biotech. Bioeng.* 23:1903–1906 (1981).
Zabriskie, D. W. et al., "Estimation of Cell Biomass and Growth Rate by Measurement of Culture Fluorescence" *Abstract of the Annual Meeting of the American Society for Microbiology* #023 (1975).
Harris, C. M. et al., *Enzyme Microb. Technol.* 9:181–186 (1987).

*Primary Examiner*—Richard A. Rosenberger
*Assistant Examiner*—Hoa Pham
*Attorney, Agent, or Firm*—Hamilton, Brook, Smith & Reynolds

[57] ABSTRACT

This invention pertains to a method and an apparatus for determining concentration of solid particles of interest in a sample in the presence of at least one other type of solid particle by measuring light scatter at a wavelength which is independent of solid particle concentration which is not of interest and related to solid particle concentration of interest. Preferably, solid particles of interest are cells grown in cell culture medium comprising a solid substrate.

18 Claims, 11 Drawing Sheets

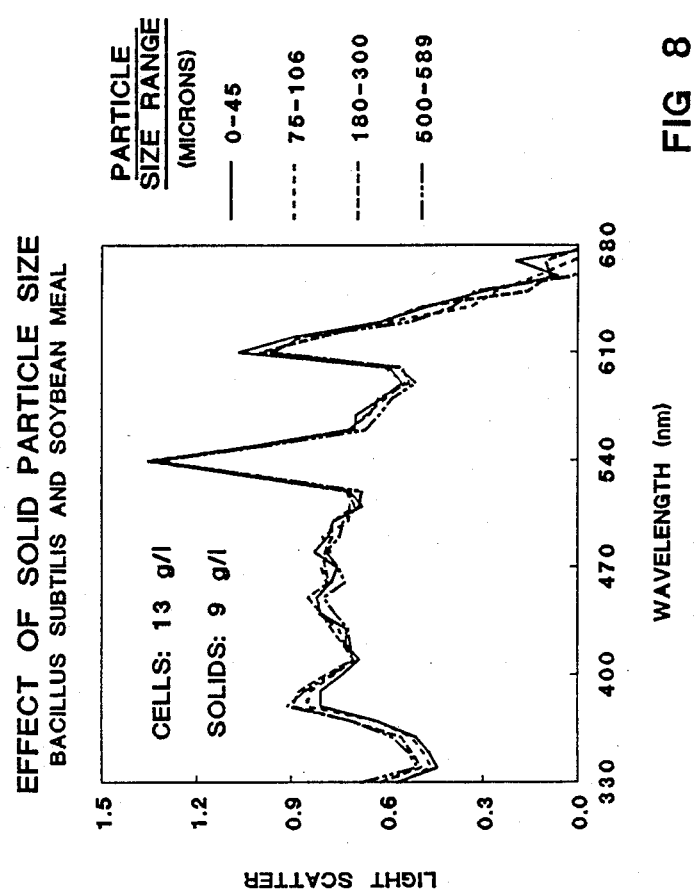

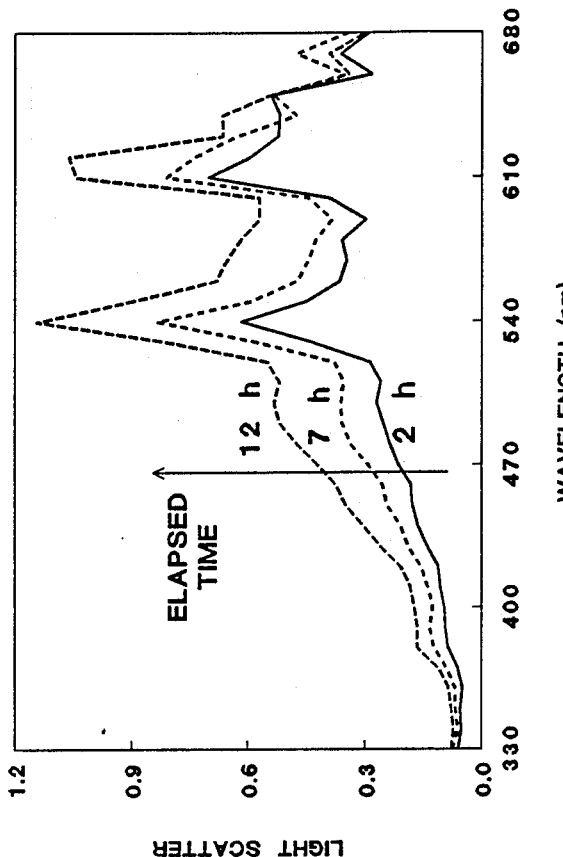

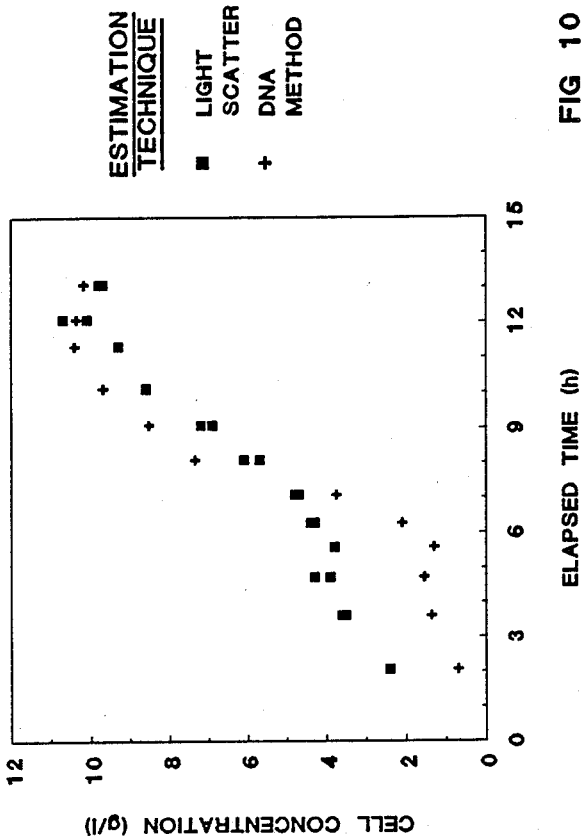

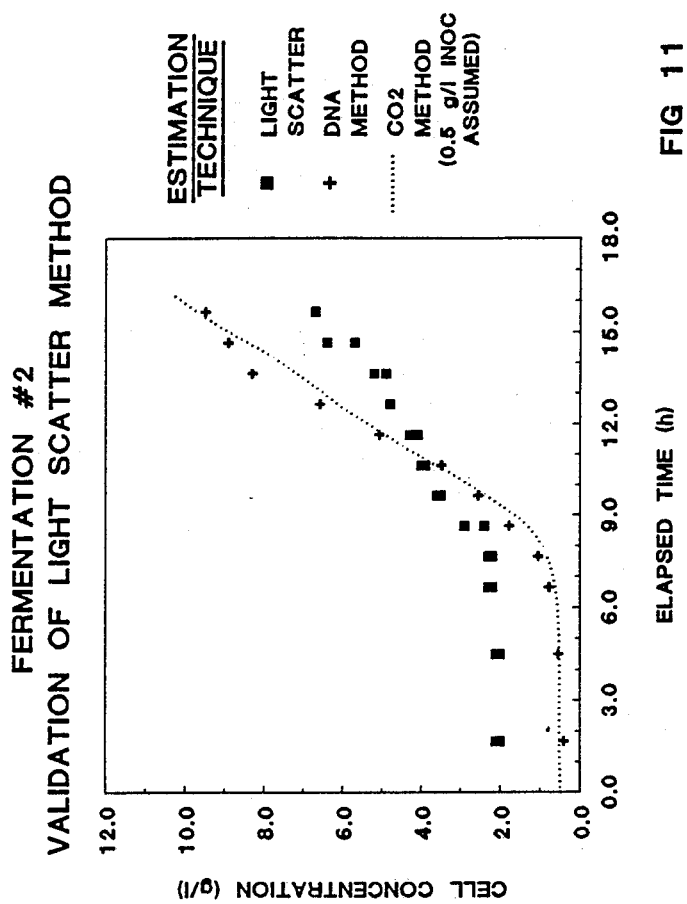

4,969,741

MEASUREMENT OF SOLID PARTICLE CONCENTRATION IN PRESENCE OF A SECOND PARTICLE TYPE

GOVERNMENT SUPPORT

The invention described herein was supported by Grant No. CDR-88-03014 from the National Science Foundation. Thus, the Government has certain rights in the invention.

BACKGROUND OF THE INVENTION

Most industrial fermentation media contain solid components. These components are either proteinaceous meals such as soybean, cottonseed and fish meal or carbohydrate based solids such as corn starch. Solid components are added to fermentation media because they provide a wide range of nutrients, (e.g., carbon nitrogen and minerals) and because they are inexpensive sources of these nutrients. Solid substrates are usually widely available as agriculture and other products.

The presence of solids in fermentation media, however, interfere with techniques for estimating cell mass concentration during the fermentation process. Several techniques, mostly indirect, have been used to estimate cell mass concentration in fermentation broths containing solid components. For example, cell mass concentration can be estimated by cell enumeration and staining techniques, cell colony counting using plating techniques, centrifugal separation, measurement of a chemical component of the cell (e.g., carbon, protein or DNA content) or measurement of some excreted product and cellular metabolism (e.g., $CO_2$, or enzyme). These techniques, however, are labor intensive, inaccurate or do not work well for all phases in a fermentation process. Moreover, many of these methods are not suitable for industrial fermentations and are difficult or impossible to use on line.

Another approach for measuring cell mass concentration is by light scattering. (Hancher, C. et. al., *Biotech Bioeng.* 16:475–484 (1974); Junker, B. et al., *Biotech. Bioeng.* 32:55–63 (1988)). Light scatter is a function of the incident light wavelength and intensity, particle size and shape and the difference in refractive indices between the particles and the suspending medium (Powell, E. O., *Journal of the Science of Food and Agriculture* 14:1–8 (1963). Junker and co-workers describe a method for measuring cell mass by integrating and correlating cell mass concentration with the amount of light scattered as a function of the incident wavelength (330–700nm). The concentration of cells grown in solid substrate fermentations was not considered by Junker et al. The major limitation of light scatter techniques is interference from background particles such as solid components of the fermentation medium.

Thus, there exists a need for a method of estimating cell mass concentration in the presence of solid components which is accurate, can be automated and used on-line.

SUMMARY OF THE INVENTION

This invention pertains to a method for determining concentration of solid particles of interest in a sample in the presence of at least one other type of solid particle which has an absorbance and/or light scatter that is a function of wavelength and which is different from that of the particles of interest. Solid particle concentration in a sample is determined by illuminating the sample at consecutive fixed wavelengths to generate a range of wavelengths. Scatter of light by the sample is measured at each wavelength over the wavelength range. An invariant region is then determined as being a region of the wavelength range at which light scatter is independent of the solid particle concentration which is not of interest and related to solid particle concentration of interest. Solid particle concentration associated with the light scattered in the invariant region is related to a predetermined relationship between light scatter and concentration of the particles of interest in the absence of the other particle type. In one embodiment, the solid particles of interest are cells grown in cell culture medium comprising a solid substrate. Using the methods of this invention, cell concentration can be determined at any stage of cell growth.

The invention further pertains to a computer-assisted system for determining concentration of one particle in a suspension of at least two distinct particles in which each particle type has independent light scatter characteristics which change as a function of wavelength.

BRIEF DESCRIPTION OF THE DRAWINGS

FIG. 8 is a graphic representation illustrating the effect of soybean meal particle size on the light scatter spectrum of *B. subtilis* and soybean meal at constant solid concentration.

FIG. 9 is a graphic representation illustrating light scatter spectra recorded at various time intervals during fermentation of *B. subtilis* and fish meal.

FIG. 10 is a graphic representation illustrating a comparison of *B. subtilis* cell concentration using light scatter and DNA techniques for estimating cell concentration during a fermentation.

FIG. 11 is a graphic representation illustrating a comparison of *B. subtilis* cell concentration using light scatter, DNA and carbon dioxide evolution techniques for estimating cell concentration during a fermentation.

DETAILED DESCRIPTION OF THE INVENTION

Figure 1:
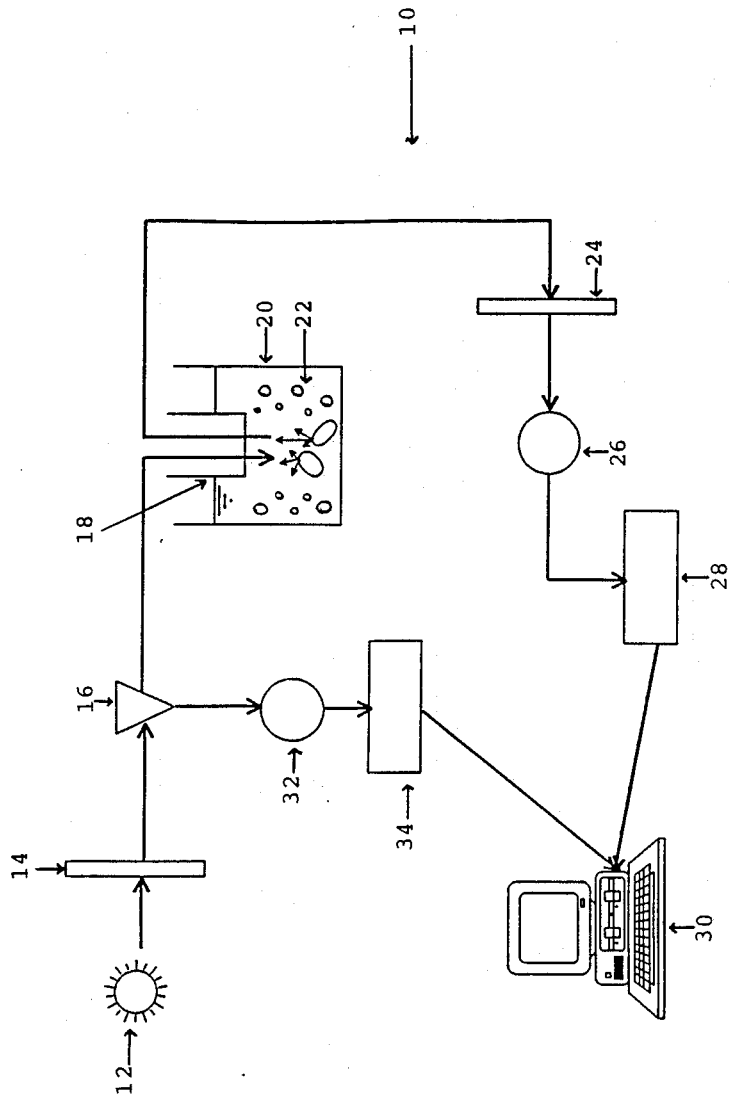
FIG. 1 is a schematic representation of a light scatter measurement apparatus according to this invention.

This invention is based upon the discovery of a region of a light scatter spectrum at which light scatter equals the amount of light absorbed by a particle and is independent of a second particle type. This discovery is based upon the principle that solid particles scatter as well as absorb light, both of which are a function of the particle concentration and incident wavelength. The present method takes advantage of these principles and provides a means for determining concentration of solid particles of interest in a sample in the presence of at least one other type of solid particle. Suspensions having at least two distinct types of particles can be used to determine the concentration of the particles of interest. However, a particle type of interest must have an absorbance which changes as a function of wavelength and which is distinct from the absorbance of the other particle types. Examples of solid particle suspensions in which cell concentrations can be determined are cell cultures grown in the presence of solid substrates; cells grown in oil in water dispersions; contaminants in liquid samples; and determination of organism concentrations in fresh water or ocean samples.

A sample means a portion of the total volume of the suspension which can either be removed and subsequently tested or can be tested in situ. In either case, the sample is a representative part of the whole. The sample can be in the form of a solid/liquid suspension or some other form, as long as the sample comprises a homogeneous and representative sampling of cells and solid substrate.

In general, concentration of solid particles of interest in a sample in the presence of at least one other type of solid particle or particles is determined by illuminating the sample at consecutive fixed wavelengths to generate a range of wavelengths. Light scattered by the sample is then measured at each wavelength over the wavelength range. From the light scatter measurements, a region of the wavelength range is determined at which light scatter is independent of solid particle concentration which is not of interest and related to solid particle concentration of interest. This region is the invariant region. A predetermined relationship is established for the invariant region between light scatter and concentration of the particles of interest in the absence of the other particle type. The solid particle concentration of interest can then be determined by measuring light scatter in the invariant region.

The invariant region is a range of wavelengths where the light scattered by a suspension comprising at least two different types of particles is independent of solid particle concentration which is not of interest but is related to solid particle concentration of interest. For example, in estimating concentration of cells grown in the presence of a solid substrate, the invariant region is the range of wavelengths whereby the light scattered by the sample is not significantly affected by the solid substrate concentration but is related directly to the cell concentration. The location of the invariant region is a function of cell concentration and provides a means for determining cell concentration during solid substrate fermentations. Methods for locating the invariant region are described in detail below.

In one embodiment, the solid particles of interest are cells grown in cell culture medium comprising a solid substrate. Cell culture is intended to include the growth and utilization of all cell types.

Although concentration of solid particle types having the properties described above can be determined by the methods of this invention, for clarity the relationship of concentration and light scatter will be illustrated in terms of cells grown on a solid substrate since both cells and solid substrate particles scatter and absorb light. The light scatter spectrum of a mixture of cells and solid is a function of the cell concentration and the solid concentration. However, this functionality varies with the incident light wavelength. At high wavelengths, towards 700 nm, solid substrate particles scatter more light than they absorb. Hence adding solid particles to a suspension of cells increases the light scatter. At low wavelengths, towards 330 nm, solid substrate particles absorb more light than they scatter. Hence adding solid particles to a suspension of, cells decreases the light scatter. The solid substrate has absorbed some of the light scattered by the cell. At some intermediate wavelength (i.e., the invariant region) the solid substrate scatters as much light as it absorbs. Thus, the light scattered at this wavelength is independent of solid substrate concentration but is a direct function of cell concentration and can be used to determine cell concentration without interference from the solid substrate particles.

In a preferred embodiment, concentration of cells grown in the presence of a solid substrate is determined by measuring light scatter intensity of a sample at consecutive fixed wavelengths to generate a range of wavelengths of incident light. This range establishes a relationship between light scatter and incident light wavelength. Such a relationship can be depicted in the form of a curve, light scatter as a function of incident light wavelength. The relationship, however, can be a set of data points generated and stored in a computer, for example. The wavelength range is then divided into intervals of equal size and the light scatter measured over each interval is summed. Each sum represents the light scatter attributed to a particular wavelength interval. In the case that a curve is established, the area under the curve for each wavelength interval is determined. This step provides a more realistic value of light scatter as a function of particle concentration at a particular wavelength.

Cell concentration for each wavelength interval is then determined by comparing light scatter for each interval with a predetermined relationship between light scatter and cell concentration in the absence of solids or second particle type. The predetermined relationship is established by a calibration or standard curve of light scatter of samples comprising varying concentrations of cells without solids present. Such a relationship can be established because light scatter by the samples is a function of wavelength and cell concentration, irrespective of the location of the invariant wavelength. Preferably, a standard curve (light scatter versus wavelength) can be produced by suspending known concentrations of cells of interest in water and determining the light scattered by the resulting suspension.

The invariant region associated with cell concentration estimated at each wavelength interval is then located. Cell concentration for each interval is compared with a predetermined relationship between cell concentration and invariant wavelength. This predetermined relationship between cell concentration and invariant wavelength is established by constructing a calibration curve of light scatter of samples comprising a known cell concentration and varying solid concentration. Preferably, light scatter spectra can be generated by first determining the light scattered by a known concentration of only cells in suspension. A known concentration of solid substrate is then added to the cell suspension and the light scatter spectrum of the resulting suspension is measured. Additional amounts of known solid substrate are added to thereby produce light scatter spectra having fixed cell concentration and varying solid particle concentration. The light scatter spectra obtained are plotted onto a single graph to determine the location of the invariant region for a known cell concentration.

A standard curve comprising four light scatter spectra is sufficient for establishing the location of the invariant region. For illustration purposes, the use of a calibration curve comprising four spectra is described. However, the number of spectra used to generate a calibration curve can vary by experimental design. The invariant region is located by using one of the following methods. The second and third methods which are described below provide the best estimation of the location of the invariant region.

A. Percentage Criteria Method

At each wavelength, the four light scatter readings are averaged and the percentage deviation of each light scatter reading (at the same wavelength) from this average are determined. The absolute values of these percentage deviations are again averaged. If the average deviation from the mean is less than 10%, then the wavelength is considered to fall within the invariant region. Although 10% deviation is used as the standard criteria for determining whether a particular wavelength falls within the invariant region, other deviations can be used without significantly affecting the wavelength location.

This method, however, tends to predict very narrow invariant regions at low cell concentrations and very wide invariant regions at high cell concentrations

B. Crossover Criteria Method

In this method, at each wavelength the light scatter reading of the cells only spectrum is compared to the three light scatter readings (at the same wavelength) obtained for the cell/solid substrate combinations. If the cells only reading is above or below the other three readings then this wavelength is not within the invariant region. However, the wavelength of the cells only reading is deemed to be within the invariant region if it is equal to or in between the other three readings. In other words, light scattered at a particular wavelength for the cell only suspension must be located between the upper and lower light scatter readings in order for it to be deemed within the invariant region.

C. Optical Criteria Method

The four standard spectra described above are plotted onto one graph. The location of the invariant region is determined visually as being the point of intersection of each light scatter spectrum. The results from this method will vary slightly with the observer but are usually within the invariant regions predicted by the above two methods.

In order to determine actual cell concentration, the wavelength for each interval of the sample is compared with the corresponding invariant wavelengths determined, as described above. If the sample wavelength is within the invariant region, then the cell concentration determined using the first calibration curve (i.e., light scatter versus cell concentration) is a valid concentration measurement. The comparison of wavelength attributed to cell concentration to the invariant region insures that light scatter is independent of solid substrate concentration. Thus, a wavelength which falls within the invariant region accurately represents the concentration of cells to be determined. A number of consecutive valid concentration measurements from the same raw spectra can be averaged to determine mean concentration for the particles of interest.

The location of the invariant region, as previously described, is dependent on cell type, cell concentration and the solid type. Extracellular enzymes will degrade the solid substrate during the fermentation. However, at constant solid concentration, the particle size of the solid has no effect on the light scattered (See FIG. 9). Interestingly, the invariant region shifts to a higher wavelength as the concentration of cells increases. Thus, a shift in the invariant region accurately predicts that there is an increase in cell concentration.

A sample can be illuminated and light scatter detected at range of wavelengths using a variable wavelength spectrophotometer or fluorimeter in combination with a probe. In one embodiment, a variable wavelength fluorimeter can be suitably adapted for measuring light scatter by setting excitation and emission wavelengths equal to each other. Preferably, the light scatter equipment will have the capacity to generate a range of wavelengths of from 190–900 nm and can have any intensity. The specific range of wavelengths, however, is dependent upon the type of particles in the sample. The intensity of the light scattered is then detected by a probe.

The probe used to detect light scatter is critical to the accuracy of the method. Preferably, the probe is a front-face fiber optic probe which measures scattered light at zero degrees. The wavelength of light leaving the probe into the sample should be equal to the wavelength of light entering the probe.

A schematic representation of a preferred detection apparatus is shown in FIG. 1. The apparatus (10) comprises a light source (12) that can provide light of variable wavelength, such as a Xenon arc lamp. The light passes directly to a excitation monochrometer (14) for selecting an excitation wavelength. Light is passed to a beam splitter (16) that divides the excitation light.

One fraction of the light passes to a fiber optic probe (18), inserted into a container (20) and a sample comprising two different particle types (22). The container (20) can be a fermentor. Light emitted from the sample passes back through the fiber optic probe (18) to an emission monochromator (24) set at a wavelength equal to the excitation wavelength. Resulting light of narrower wavelength passes to an emission photomultiplier (26), which produces a current that is proportional to emission light intensity entering the photomultiplier (26). The current is passed to an emission radiometer (28) where the current is amplified. The current signal is transformed into a digital signal and sent to a computer (30).

The other fraction of light passing through the beam splitter (16) goes to an excitation photomultiplier (32) that produces a current proportional to excitation light intensity. The current is then passed through an excitation radiometer (34) which amplifies the current. The amplified current is then detected by the computer (30). The computer permits on-line computer analysis and control.

The light scatter readings are the ratio of current produced by the excitation radiometer (34) to the current produced by the emission radiometer (28). The ratio is unitless. This ratio avoids the variations in source light intensity as a function of wavelength and the decreased intensity of the source as a function of time.

This invention also pertains to an apparatus for measuring concentration of solid particles of interest in a sample in the presence of at least one other type of solid particle. The apparatus will comprise a means for illuminating the sample at variable wavelength (e.g. spectrophotometer or fluorimeter); a means for detecting light scatter intensity at variable wavelengths and a computer means for monitoring and determining solid particle concentration. Optionally, the system can comprise a means for removing a representative sample from the whole. One or more computer means are employed to determine solid particle concentration by the methods of this invention. In particular, the computer is programmed to measure light scatter intensity of the sample at a wavelength at which light scatter is independent of solid particle concentration which is not being determined and related to solid particle concentration of interest. Since this exact wavelength region is not known in advance, a wide range of wavelengths must be measured. Concentration of the solid particles of interest are related to a predetermined relationship between light scatter and concentration of particles of interest in the absence of the other particle type.

This invention can be useful in a number of applications in which different types of solid particles can be distinguished from each other. The particle types, however, must have the properties described above. The invention could be used to monitor the growth of filamentous organisms (e.g., mold or actinomycetes) on solids, growth of mixed cell cultures, to detect cellular matter for treatment of waste water and fresh water ponds (e.g., algae). The invention can also be used in the field of oceanography for determining cellular mass.

The invention will be further illustrated by the following examples.

EXAMPLE 1

Light Scatter Equipment

Light scatter was measured using a fluorimeter made from components supplied by the Oriel Corporation (Stratford, CT). A schematic diagram of the equipment is shown in FIG. 1 and has been shown in Junker, B. H. "Monitoring and Assessment of Aqueous/Perfluorocarbon Fermentation Systems", Ph.D. thesis, Massachusetts Institute of Technology, (1988) and Junker, B. H., et al. Biotechnology and Bioengineering, 32:55-63, (1988). The excitation monochromator (slit width 5 nm) and emission monochromator (slit width 20 nm) wavelengths were set equal to each other to measure light scatter. The light source was a 150 Watt Xenon arc lamp. The fiber optic probe used was a front faced probe (model #77558, Oriel Corporation) which measured the light scattered at zero degrees to the incoming light. The bias voltage for the excitation photomultiplier was 300 volts and for the emission photomultiplier 800 volts. The fluorimeter was controlled by computer using Oriel fluorescence spectrophotometry system software version 1.1 (Oriel Corporation and Massachusetts Institute of Technology, 1988). After amplification, the current signals were transformed into a digital signal and sent to an APPLE IIE computer.

EXAMPLE 2

Light Scatter Spectra of Cells Only

*Bacillus subtilis* var *sakainensis* (ATCC 21394; U.S. Pat. No. 3,622,458) was grown in a BIOFLO 2 microprocessor controlled bench scale fermenter (New Brunswick Scientific Co., Inc., Edison, New Jersey) on glucose, nutrient broth, trace minerals and antifoam. pH was controlled by the addition of a base. After a period of growth, the cells were harvested and left to sediment overnight at 4° C. The cell sediment was then centrifuged to obtain a cell paste consisting of packed cells at a concentration of approximately 230 g/l. The concentration of the cell paste was later accurately determined by drying a known weight of wet cells for 48 h at 60° C. This cell paste was then diluted with water to give the cell concentrations 5, 9, 13 and 17 g/l.

100 mls of a sample of known cell concentration, along with a magnetic stirring bar, was placed in a glass beaker painted black on the outside. Light scatter was determined using the light scatter equipment shown in FIG. 1. The front face fiber optic probe was then placed into the beaker with the tip of the probe submerged to a depth of 1 cm. The entire beaker plus probe was wrapped in tin foil to prevent stray light reaching the sample and probe. The wrapped assembly was placed on a magnetic stirrer and the sample was agitated vigorously. The light scatter spectrum of the sample was then obtained by taking a light scatter reading every 10 nm between 330 and 700 nm. Each reading comprised the average of a series of readings taken over a one second interval. A complete spectrum over this wavelength range was generated in 3 minutes 20 seconds.

Figure 2:
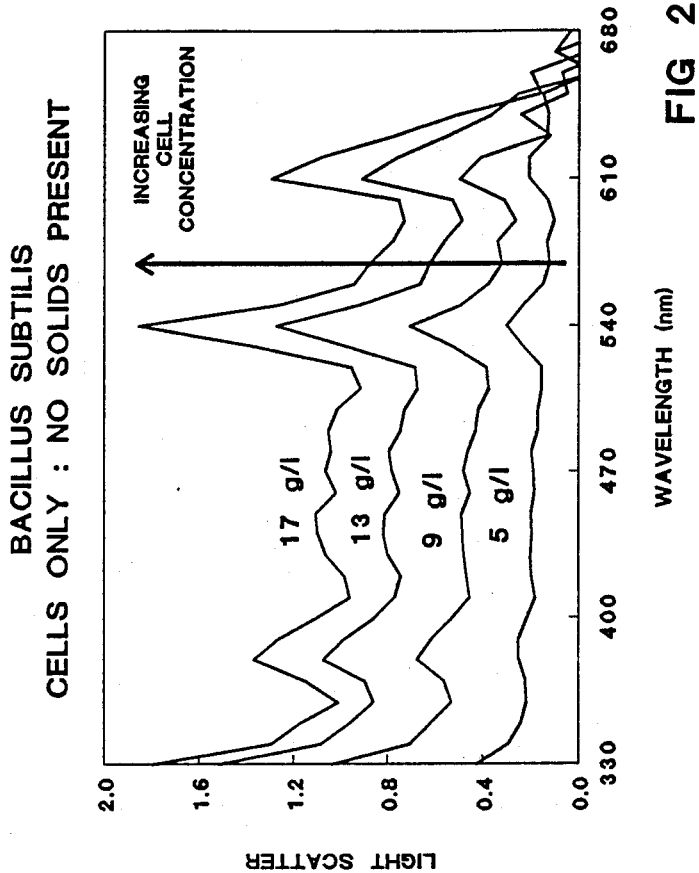
FIG. 2 is a light scatter spectra of *Bacillus subtilis* cells suspended in water.

FIG. 2 shows the light scatter spectra of various concentrations of cells suspended in water (not fermentation media) and the relationship of light scatter to cell concentration. This figure represents the first set of which calibration data was used to predict the cell concentration after the light scatter at the invariant region was determined.

EXAMPLE 3

Light Scatter Spectra of Cells (1.9 g/l) and Solids at Increasing Concentration A cell paste was prepared using the same method as in Example 2. This cell paste was diluted with water to give a cell concentration of 1.9 g dry cell weight/l. The light scatter spectrum of 100 mls of the solution containing cells was measured as described in Example 2.

After the light scatter spectrum was measured, fish meal was added to the solution containing cells to give a fish meal concentration of 9 g dry weight/l. The light scatter spectrum was then measured again. Additional fish meal was added to the same sample to give a fish meal concentration in the sample of 18 g dry weight/l and the light scatter measured. The process was repeated to yield a final fish meal concentration in the sample of 27 g/l.

Figure 3:
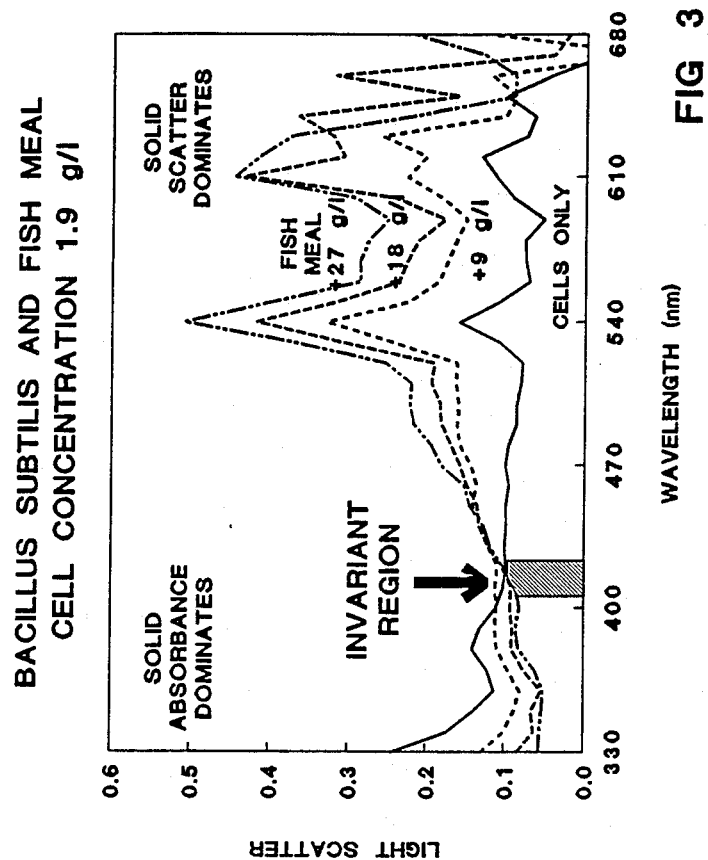
FIG. 3 is a light scatter spectra of *B. subtilis* cells (1.9 g/l) and various concentrations of fish meal, illustrating an invariant region.

FIG. 3 shows the light scatter spectra of the four samples. Each sample has approximately the same cell concentration but a different solid substrate concentration. The figure shows the existence of an invariant region and its location. This figure was used to estimate the location of the invariant region at a given cell concentration. The intersection of these four curves marks the existence of an invariant region. The width of the invariant region at this cell concentration was identified using one of the methods described in the Detailed Description of the Invention.

EXAMPLE 4

Light Scatter Spectra of Cells (13.5 g/l) and Solids at Increasing Concentration The method is similar to that described in Example 3 except that the cell paste was diluted to 13.5 g dry cell weight/l instead of 1.9 g dry cell weight/l.

Figure 4:
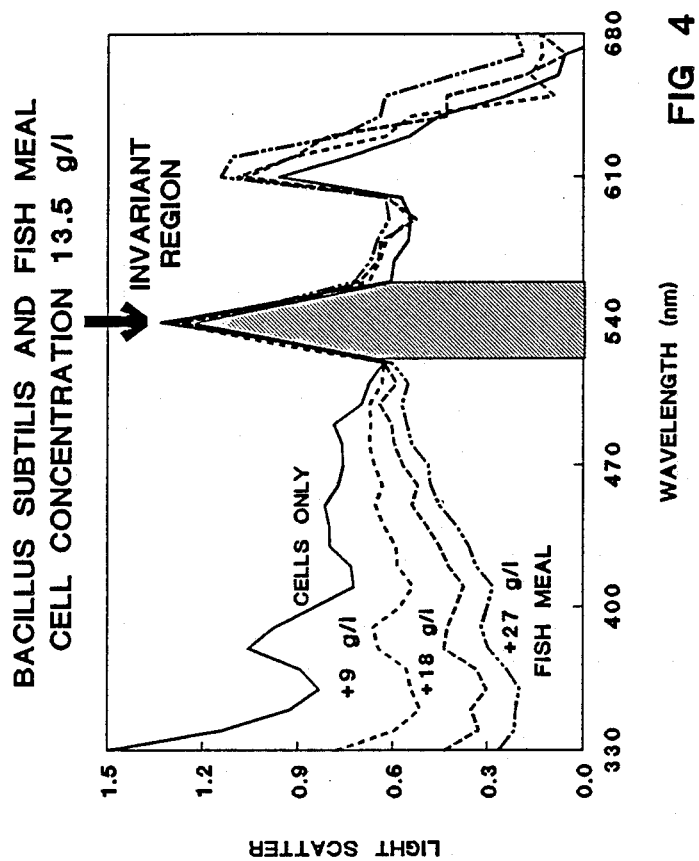
FIG. 4 is a light scatter spectra of *B. subtilis* (13.5 g/l) and various concentrations of fish meal illustrating an invariant region.

FIG. 4 shows the light scatter spectra of the samples having a higher cell concentration than the samples shown in Example 3. The location of the invariant region was approximately 540 nm. In contrast, the invariant region for a sample containing a lower cell concentration was around 420 nm (FIG. 3). The upward shift in location of the invariant region when cell concentration was increased indicated that the location of the invariant region was dependent on cell concentration.

EXAMPLE 5

Location of the Invariant Region

This experiment was performed similar to those described in Examples 3 and 4 but at different cell concentrations ranging from approximately 1–18 g dry cell weight/l. For each given cell concentration the location of the invariant region was determined using the crossover criteria method previously described. The center of the invariant region was then plotted as a function of the cell concentration.

Figure 5:
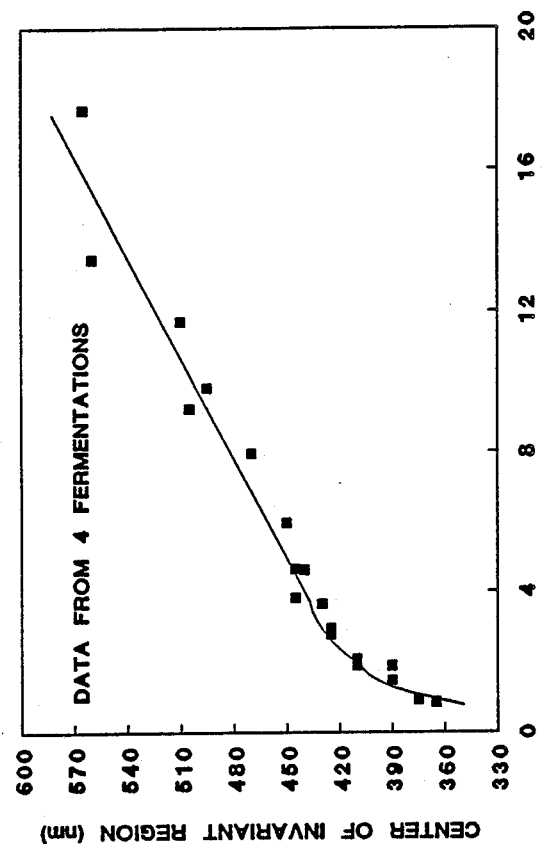
FIG. 5 is a graphic representation of the location of the invariant region as a function of cell concentration for *B. subtilis* and fish meal illustrating an invariant region.

FIG. 5 shows the location of the center of the invariant region as a function of cell concentration. Data on the width and location of the invariant region at each cell concentration represent the second set of calibration data which was used to identify the location of the invariant region in a fermentation sample of unknown cell concentration.

EXAMPLE 6

Invariant Region Between *Bacillus Subtilis* and Soybean Meal

Figure 6:
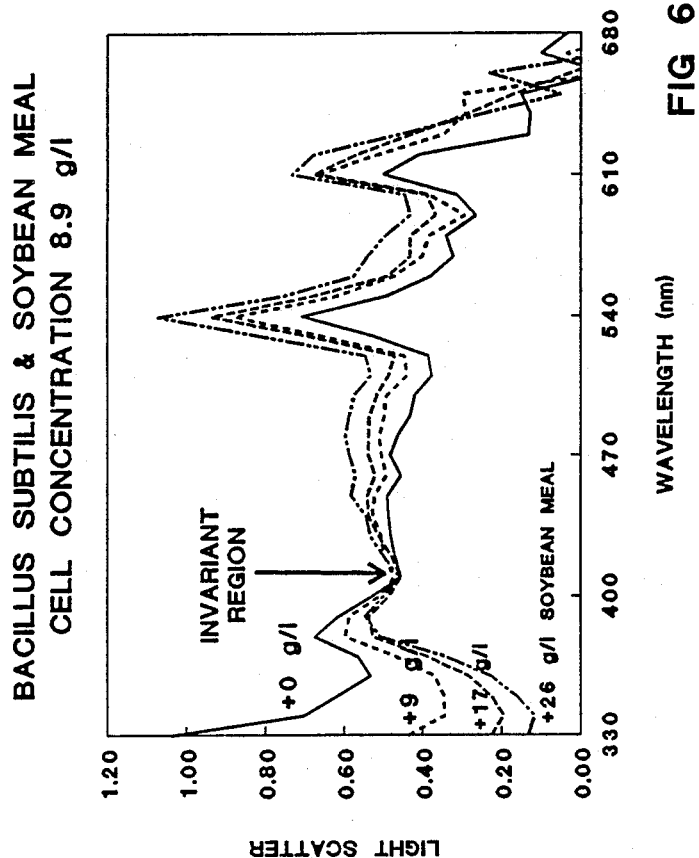
FIG. 6 is a light scatter spectra of *B. subtilis* cells (8.9 g/l) and soybean meals illustrating an invariant region.

The method used to produce the data shown in FIG. 6 was the same as described in Examples 3 and 4 except the cell concentration was 8.9 g dry cell weight/l and soybean meal was used instead of fish meal. Soybean meal concentrations of 0, 9, 17 and 26 g dry weight/l were used. Soybean meal was obtained from Ventura Grain Inc., 148 Longmeadow Road, Taunton, MA 02780.

FIG. 6 shows an invariant region between *Bacillus subtilis* var *sakainensis* (ATCC 21394) and soybean meal. The figure shows that the invariant region was present when other solid substrates were used and is, therefore, not a phenomenon strictly associated with fish meal.

EXAMPLE 7

Invariant Region Between Baker's Yeast and Fish Meal

Figure 7:
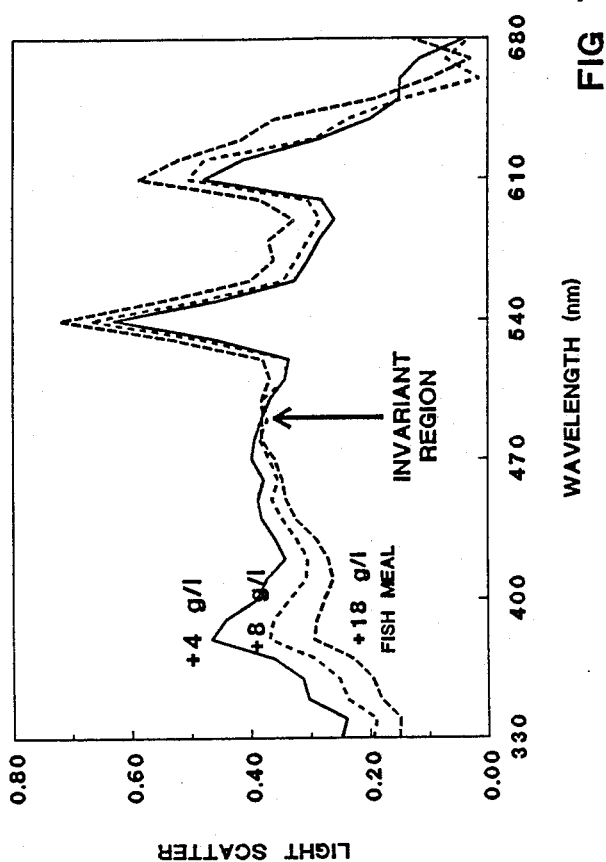
FIG. 7 is a light scatter spectra of *Saccharomyces cerevisiae* (Baker's Yeast) and fish meal showing an invariant region.

The methods used to determine the invariant region between Baker's Yeast and fish meal are described in Examples 3 and 4. Baker's Yeast was grown in synthetic medium. Fish meal concentrations of 4, 8 and 18 g dry weight/l and a cell concentration of 10.9 g dry cell weight/l were used. The light scatter spectra of the and the invariant region between *Saccharomyces cerevisiae* (Baker's yeast) and fish meal is shown in FIG. 7. The figure shows that an invariant region can be obtained for cell types other than *Bacillus subtilis*.

EXAMPLE 8

Effect of Solid Particle Size on the Light Scatter Readings

A cell paste was prepared as described in Example 2. This cell paste was diluted with water to give a cell concentration of 13 g dry cell weight/l. Four 100 ml samples of this cell concentration were prepared. Soybean meal was added to each sample to give a final soybean meal concentration in each sample of 9 g dry weight/l. The difference between samples was that each sample contained soybean meal of a different particle size range. The different particle size ranges shown in FIG. 8 were prepared by taking whole soybean meal as supplied by Ventura Grain Inc. (148 Longmeadow Road, Taunton, MA 02780) and sieving them into the various size fractions.

FIG. 8 shows the effect of solid particle size on the light scatter readings obtained from a mixture of cells and solids at constant solid concentration (weight basis). The light scatter readings were not affected by a decrease in solid substrate particle size.

EXAMPLE 9

Fermentation Time Profile of *Bacillus Subtilis* Grown in Fish Meal

*Bacillus subtilis* var *sakainensis* (ATCC 21394) was grown on a mixture of fish meal (30 g dry weight/l), glucose (15 g/l), potassium phosphate dibasic (1.3 g/l), magnesium sulphate septahydrate (0.5 g/l). pH was controlled by adding sodium hydroxide (250 g/l). Foaming was controlled by adding polypropylene glycol when required. Glucose solution (400 g/l) was also added in a feed batch manner during the fermentation. After 2 hours a 100 ml sample was removed from the fermenter and transferred to a beaker painted black. The light scatter spectrum of this sample was then measured as described in Example 2. This process was repeated at 7 and 12 hours.

FIG. 9 shows light scatter spectra recorded at various time intervals during the fermentation of *Bacillus subtilis* on fish meal.

EXAMPLE 10

*Bacillus Subtilis* Fermentation #1

*Bacillus subtilis* was grown as described in Example 9. A 100 ml sample was taken at approximately every hour throughout the fermentation. The light scatter spectrum of the sample was then obtained as described in Example 9. For each sample taken, the light scatter spectrum was obtained in duplicate.

The area under each light scatter spectrum was then integrated in 10 nm intervals (e.g., 330–340 nm, 340–350 nm, etc.). The area under each 10 nm interval was compared to the corresponding area under the spectra of FIG. 2 (cells only). The cell concentration was estimated for each wavelength interval.

At each wavelength interval, the cell concentration prediction was compared to the cell concentration range that would be expected if the invariant region was indeed at this wavelength interval. If the cell concentration prediction did fall within the invariant region, then this cell concentration prediction was assumed valid. This process was repeated at each wavelength interval throughout the entire obtained spectrum. Valid concentration estimates at consecutive wavelengths were averaged to give the final light scatter cell concentration estimate. Such estimates were then plotted as a function of time.

Cell concentration was also estimated by determining DNA content. For the DNA estimates, 10 ml sample of fermentation broth was centrifuged and washed using deionized water. The centrifugation and washing process was repeated four times. This left a pellet of cells and residual fish meal. The pellet was suspended in water and sonicated for 7 minutes to rupture the cells. The cellular homogenate was separated from the cell debri and fish meal by centrifugation and then by filtration through a 0.22 micron filter. The DNA content of the cellular homogenate was determined according to Brunk, C. et al., *Analytical Biochemistry*, 92:497–500, (1979).

The DNA content of the fermentation sample was compared to the DNA content of a standard sample of cells of known concentration grown with no solid substrate present as described in Example 2. From this comparison, a cell concentration could be estimated.

FIG. 10 shows a comparison of results obtained using the light scatter technique and using the DNA technique for estimating cell concentration during a fermentation. Both the DNA and the light scatter curves follow the same trend.

EXAMPLE 11

*Bacillus Subtilus* Fermentation #2

The data in this experiment was generated as described in Example 10 except that the fermentation medium initially contained 40 g dry weight fish meal/l and 20 g/l glucose instead of the 30 g dry weight fish meal/l and 15 g/l glucose used in Example 9.

The carbon dioxide evolution method was used to estimate cell concentration by measuring the total amount of carbon dioxide evolved during the fermentation. A standard correlation of 34.1 mmoles carbon dioxide l/g cell was used to convert the total carbon dioxide evolved into a cell concentration estimate. This standard correlation was determined by growing *Bacillus subtilis* var *sakainensis* (ATCC 21394) as described in Example 2 and measuring both the dry cell weight and the total amount of carbon dioxide evolved.

In using the carbon dioxide evolution technique to determine the cell concentration in the fermenter, the cell concentration at the beginning of the fermentation must be known. The initial cell concentration, however, could not be determined because the inoculum to this fermentation also contained solid substrate.

FIG. 11 shows how the light scatter technique compares to a DNA technique and a carbon dioxide evolution technique for estimating cell concentration. In the results shown in FIG. 11, an initial cell concentration in the fermenter of 0.5 g dry cell weight/l was assumed. The DNA method and the carbon dioxide evolution techniques are both inaccurate methods for estimating cell concentration due to limitations inherent in these methods. The DNA technique is inaccurate because the DNA content of *Bacillus subtilis* is a function of growth rate of the cell. The limitation of the carbon dioxide evolution technique is that some carbon dioxide evolved may be associated with product formation and not with cell growth.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of measuring concentration of solid particles of interest in a sample in the presence of at least one other type of solid particle which has an absorbance that is a function of wavelength and that is different from the absorbance of the particles of interest, comprising the steps of:
   (a) illuminating the sample at consecutive fixed wavelengths to generate a range of wavelengths;
   (b) measuring scatter of light by the sample at each wavelength over the wavelength range;
   (c) determining a region of the wavelength range at which light scatter is independent of solid particle concentration which is not of interest and related to solid particle concentration of interest; and
   (d) relating the wavelength region determined in (c) with a predetermined relationship between light scatter and concentration of the particles of interest in the absence of the other particle type to thereby obtain the solid particle concentration of interest.

2. The method of claim 1, wherein light scatter is measured using a front face fiber optic probe.

3. The method of claim 2, wherein the solid particles of interest are cells.

4. A method of measuring concentration of solid particles of interest in a sample in the presence of at least one other type of solid particle which has an absorbance that is a function of wavelength and that is different from the absorbance of the particles of interest, comprising the steps of:
   (a) measuring the light scatter intensity of a sample at consecutive fixed wavelengths to generate a range of wavelengths of incident light, to thereby establish a relationship between light scatter intensity and incident light wavelength;
   (b) dividing the range of wavelengths into intervals of equal size and summing the measured light intensity over each interval;
   (c) determining concentration of the particles of interest for each interval by comparing light scatter for an interval with a predetermined relationship between light scatter and concentration of the particles of interest in the absence of the other particle type;
   (d) determining for each concentration determined in step (c), the invariant wavelength for the concentration of the particle of interest with a predetermined relationship between concentration of the particles of interest and invariant wavelength; and
   (e) comparing the wavelength of each interval in step (c) with corresponding invariant wavelength determined in step (d) to determine if the two are the same, a determination the two are the same indicating that the concentration of the particles of interest determined in (c) is a valid measurement.

5. The method of claim 4, wherein light scatter is measured using a front face fiber optic probe.

6. The method of claim 5, wherein the sample is illuminated using a variable wavelength fluorimeter having excitation and emission wavelengths set equal to each other.

7. The method of claim 6, further comprising the step of determining a mean value for valid measurements determined at consecutive wavelengths.

8. A method of measuring concentration of cells dispersed in a sample of cell culture medium in the presence of solid substrate which has an absorbance that is a function of wavelength and that is different from the absorbance of the cells, comprising the steps of:
   (a) illuminating the sample at consecutive fixed wavelengths to generate a range of wavelengths;
   (b) measuring scatter of light by the sample at each wavelength over the wavelength range; determining a region of the wavelength range at which light scatter is independent of solid substrate concentration and related to cell concentration; and
   (d) relating the wavelength region determined in (c) with a predetermined relationship between light scatter and cell concentration in the absence of the solid substrate to thereby obtain the cell.

9. The method of claim 8, wherein light scatter is measured using a front face fiber optic probe.

10. The method of claim 9, wherein the sample is illuminated using a fluorimeter having excitation and emission wavelengths set equal to each other.

11. A method of measuring concentration of cells dispersed in a sample of cell culture medium in the presence of solid substrate which has an absorbance that is a function of wavelength and that is different from the absorbance of the cells, comprising the steps of:
   a. measuring light scatter intensity of the sample at consecutive fixed wavelengths to generate a range of wavelengths of incident light, to thereby establish a relationship between light scatter intensity and incident light wavelength;
   b. dividing the range of wavelengths into intervals of substantially equal size and summing the measured light scatter intensity over each interval;
   c. determining the cell concentration for each interval by comparing light scatter for an interval with a predetermined relationship between light scatter and cell concentration in the absence of solids;
   d. determining for each cell concentration determined in step (c), the invariant wavelength for the cell concentration by comparing cell concentration with a predetermined relationship between cell concentration and invariant wavelength; and
   e. comparing the wavelength of each interval in step (c) with the corresponding invariant wavelength determined in step (d) to determine if the two are the same, a determination that the two are the same indicating that the cell concentration determined in (c) is a valid measurement.

12. The method of claim 11, wherein light scatter is measured using a front face fiber optic probe.

13. The method of claim 12, wherein the sample is illuminated using a variable wavelength fluorimeter having excitation and emission wavelengths set equal to each other.

14. The method of claim 13, further comprising the step of determining the mean value for valid measurements determined at consecutive wavelengths.

15. An apparatus for measuring concentration of solid particles of interest in a sample in the presence of at least one other type of solid particle which has an absorbance that is a function of wavelength and that is different from the absorbance of the particles of interest, comprising:
   a. means for illuminating the sample at variable wavelengths;
   b. means for detecting light scatter intensity at variable wavelengths; and
   c. computer means for monitoring and determining solid particle concentration, wherein said computer means being programmed to illuminate the sample and measure light scatter intensity of the sample at a wavelength at which light scatter is independent of solid particle concentration which is not of interest and related to solid particle concentration of interest.

16. The apparatus of claim 15, wherein the means for illuminating the sample is a fluorimeter having excitation and emission wavelengths set equal to each other.

17. The apparatus of claim 16, wherein the means for detecting light scatter intensity is a front face fiber optic probe.

18. A method of measuring concentration of cells dispersed in a sample of cell culture medium in the presence of solid substrate which has an absorbance that is a function of wavelength and that is different from the absorbance of the cells, comprising the steps of:
   a. determining an invariant region associated with light scatter of the solid substrate;
   b. illuminating the sample within the invariant region;
   c. detecting light scatter of the sample within said region; and
   d. relating light scatter to cell concentration.

* * * * *